United States Patent [19]
Harrison

[11] Patent Number: 5,392,918
[45] Date of Patent: Feb. 28, 1995

[54] STERILE PACKAGING INCLUDING A TRAY AND A HOLDER FOR A INTRAVASCULAR GUIDE-WIRE AND A VASCULAR PUNCTURE CLOSURE SYSTEM

[75] Inventor: Howard J. Harrison, West Chester, Pa.

[73] Assignee: Kensey Nash Corporation, Exton, Pa.

[21] Appl. No.: 131,846

[22] Filed: Oct. 4, 1993

[51] Int. Cl.6 .............................................. B65D 71/00
[52] U.S. Cl. .................................... 206/571; 206/364; 206/370; 206/438
[58] Field of Search ............... 206/363, 364, 369, 370, 206/467, 470, 438, 571

[56] References Cited
U.S. PATENT DOCUMENTS

| | | | |
|---|---|---|---|
| 3,111,220 | 11/1963 | Bostrom | 206/470 X |
| 4,016,972 | 4/1977 | Szamborski | 206/470 X |
| 4,216,860 | 8/1980 | Heimann | 206/370 |
| 4,366,901 | 1/1983 | Short | 206/364 X |
| 4,676,446 | 6/1987 | Ciocarelli et al. | 206/470 X |
| 4,697,703 | 10/1987 | Will . | |
| 4,811,847 | 3/1989 | Reif et al. . | |
| 4,823,167 | 4/1989 | Manska et al. | 206/571 X |
| 4,844,249 | 7/1989 | Coulombe . | |
| 4,925,448 | 5/1990 | Bazaral . | |
| 4,979,616 | 12/1990 | Clanton . | |
| 5,031,775 | 7/1991 | Kane . | |
| 5,125,417 | 6/1992 | Nebenzahl . | |
| 5,148,920 | 9/1992 | Walker . | |
| 5,165,540 | 11/1992 | Forney . | |
| 5,193,679 | 3/1993 | White . | |

Primary Examiner—Bryon P. Gehman
Attorney, Agent, or Firm—Caesar, Rivise, Bernstein, Cohen & Pokotilow, Ltd.

[57] ABSTRACT

A sterile package for holding a vascular puncture closure system including an elongated flexible guide-wire. The package comprises a tray, a cover, and a holder for the guide-wire. The tray is formed of a self-supporting plastic material and includes a hollow central interior portion with a flange extending thereabout. A plurality of recesses are provided in the tray to hold respective ones of the components making up the closure system. A pair of retaining tabs are located on opposite sides of the hollow central interior and project slightly thereover. The holder is sealed and includes an interior arcuate raceway for holding the guide-wire in a coiled configuration with one end extending out of a small access port in the holder. The holder is arranged to be releasably held under the tabs onto the tray. The cover is arranged to be releasably secured by a heat seal to the peripheral flange of the tray over the holder. The tray is somewhat flexible to enable it to be flexed slightly to release the holder from under the tabs after the cover has been removed from the tray to release the holder from the package so that upon inversion of the tray the components drop out on to a table. The catheter can be readily removed from the holder by pulling on its distal end portion. After use the guide-wire can be reinserted into the holder for safe disposal.

16 Claims, 6 Drawing Sheets

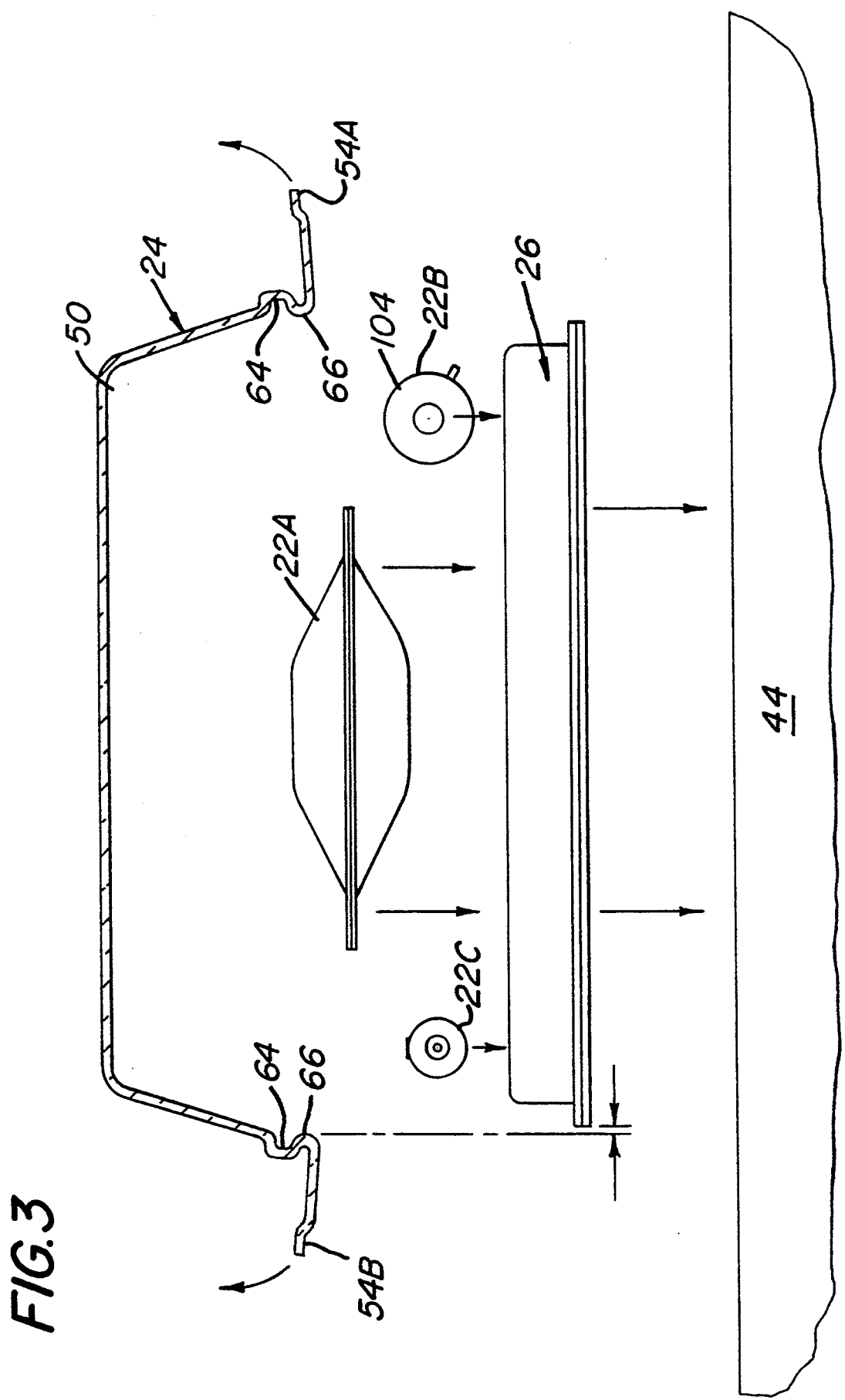

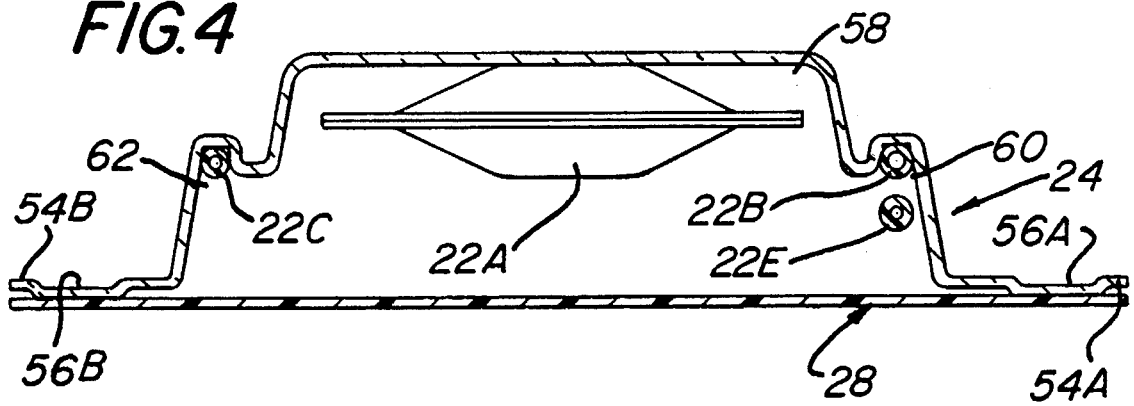
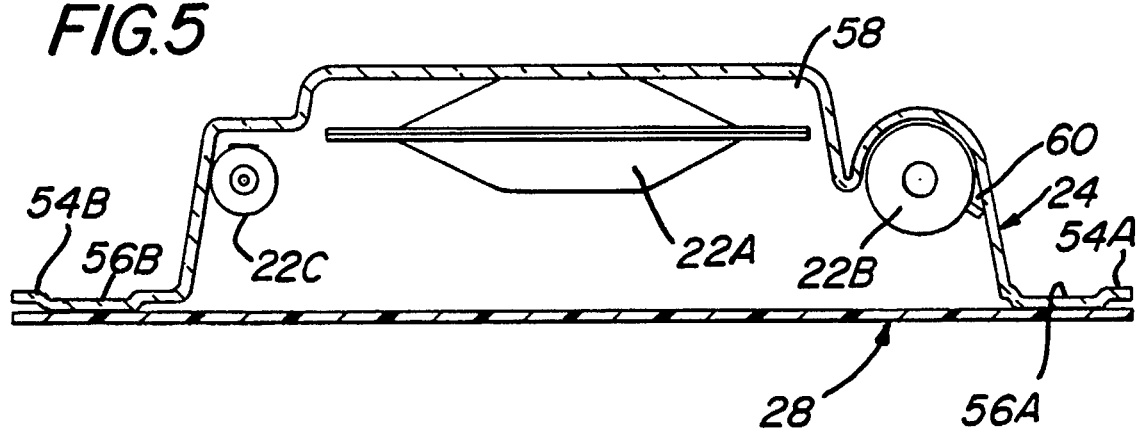
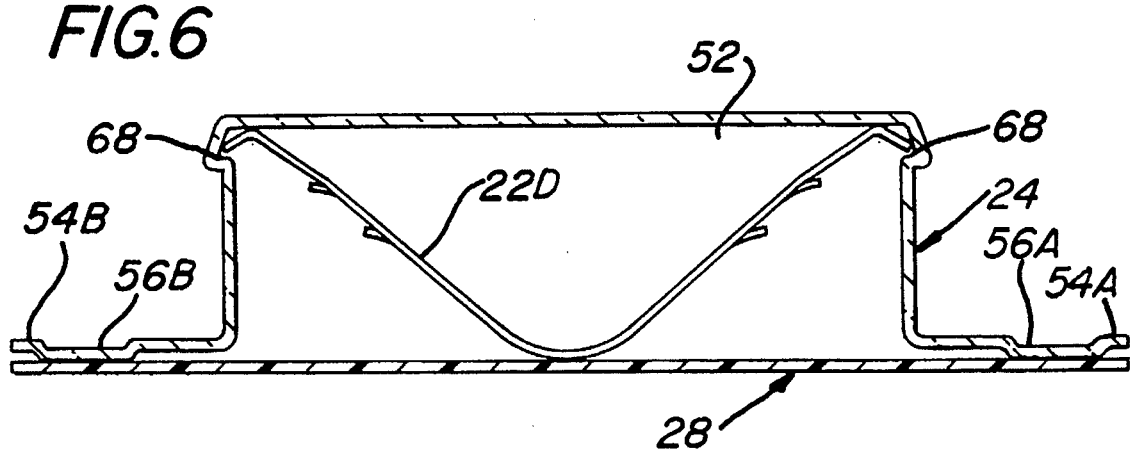

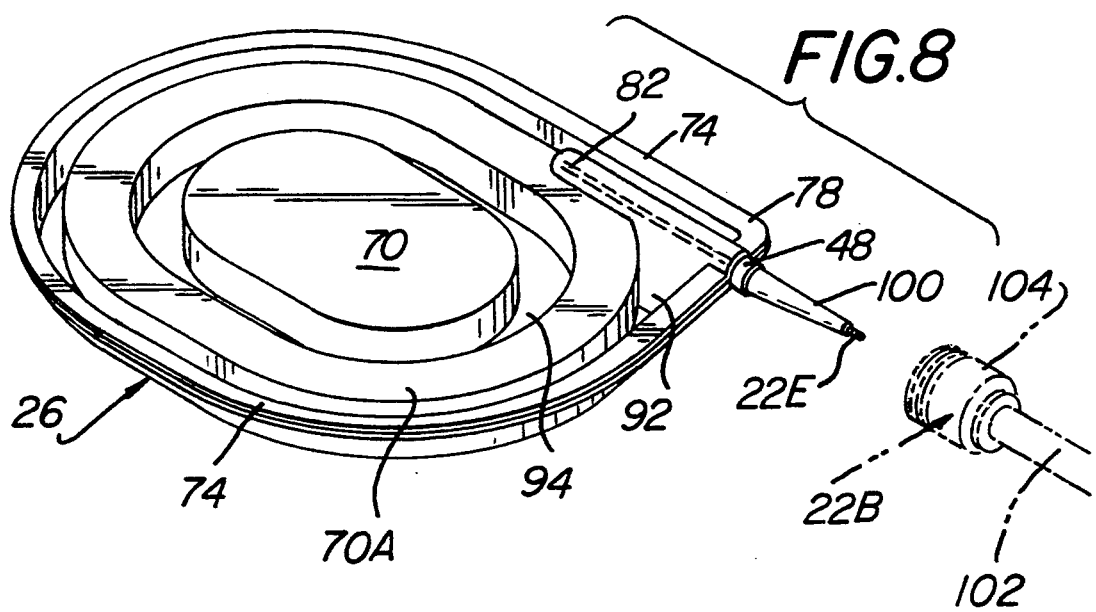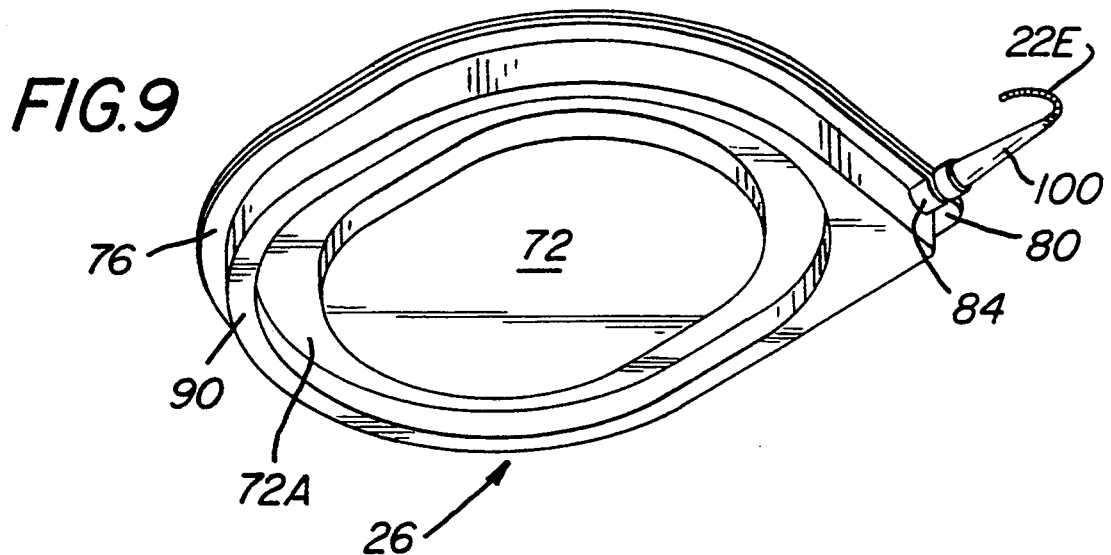

STERILE PACKAGING INCLUDING A TRAY AND A HOLDER FOR A INTRAVASCULAR GUIDE-WIRE AND A VASCULAR PUNCTURE CLOSURE SYSTEM

SPECIFICATION

This invention relates generally to packaging and more particularly to sterile packaging medical components.

BACKGROUND OF THE INVENTION

Various sterile packages have been proposed in the patent literature and many are commercially available for holding various medical components or instruments use for surgical procedures. One typical type of packaging consists of molded or thermo-formed sterilized plastic containers holding the components therein and itself being disposed within a sealed sack or flexible material pouch, so that the pouch can be opened in the operating room and the packaging placed on a sterile field to be opened to provide access to components therein. Examples of such packages are shown in the following U.S. Pat. Nos.: 4,697,703 (Will), 4,844,249 (Coulombe), 4,979,616 (Clanton), 5,148,920 (Walker), 5,165,540 (Forney), and 5,193,679 (White).

Guide-wires, catheters, and other elongated flexible medical devices for intravascular or other intralumen procedures have heretofore been packaged in various types of sterile plastic packaging for holding the elongated member in a compact, e.g., coiled, configuration. Examples of such packaging is found in the following U.S. Pat. Nos. 4,925,448 (Bazaral), 4,811,847 (Reif et al.), 5,031,775 (Kane), and 5,125,417 (Nebenzahl et al.).

The above described prior art packaging, while generally suitable for its intended purposes, nevertheless leaves something to be desired from the standpoints of simplicity of construction, ease of use, ease of loading with medical components (particularly very long flexible devices), and safe disposal.

OBJECTS OF THE INVENTION

Accordingly, it is a general object of this invention to provide a holder a very long, flexible, medical component or device which overcomes the disadvantages of the prior art.

It is another object of this invention to provide a holder for a very long, flexible, medical component or device, e.g., a guide-wire, which is constructed to enable the component to be readily loaded therein to be held in a compact configuration, to be readily removable from the holder for use, and to be readily reinserted within the holder for easy and safe disposal.

It is a further object of this invention to provide a sterile package for holding a sterile elongated intravascular or intralumen member or device, e.g., a guide-wire, and other sterile medical devices, e.g., a vascular puncture closure system including a closure and deployment components, therein.

It is still a further object of this invention to provide a sterile, sealed package for surgical devices or components which is readily openable to provide easy access to those components.

It is still a further object of this invention to provide a sterile package for surgical devices or components, at least one of which is in the form of a very elongated flexible member, e.g., a guide-wire, and which includes a separate holder for the elongated flexible member, such that when the package is opened ready access is provided to the holder to enable the removal of the elongated flexible member therefrom.

It is yet a further object of this invention to provide a method of providing an elongated medical device in a holder so that it can be readily removed for use within the body of a being where it will be exposed to a body fluid, and after use to be readily reinserted within the holder for safe disposal.

SUMMARY OF THE INVENTION

These and other objects of this invention are achieved by providing a sterile holder for holding a long, small diameter, flexible, medical component, e.g., a guide-wire, in a coiled configuration therein. The holder comprises a upper section and a lower section. Each of the sections is generally planar and has an arcuate recess therein. The sections are secured together with the recess of one of the sections being disposed within the recess of the other of the sections to form a continuous arcuate raceway between them. The holder includes an access port to the raceway and which communicates with the ambient surroundings. The access port is slightly larger in diameter than the diameter of the flexible member to enable the flexible member to be introduced therethrough and into the arcuate raceway to coil up within the raceway.

In accordance with another aspect of this invention a sterile package containing the holder with the guide-wire therein plus other sterile medical components, e.g., a closure for sealing a percutaneous incision or puncture in an artery and deployment devices therefor, is provided. The package provides ready access to those components and basically comprises a tray, a cover member, and the holder.

The tray is self-supporting and has a hollow interior portion, a peripheral flange extending thereabout, and plural retaining members projecting inwardly toward the hollow interior portion for releasably securing the holder in the hollow interior portion.

The cover is arranged to be releasably secured to the peripheral flange of the tray over said holder to seal the components within the package. The cover is releasable from the base member to expose the hollow interior of the package.

The base member is somewhat flexible to enable it to be flexed to release the holder from the retaining members after the cover is removed from the base member. The holder can then be removed from the tray, e.g., by inverting it so that the holder drops out. The elongated flexible member may then be withdrawn from the holder by grasping the holder in one hand and pulling on the elongated flexible member with the other hand.

In accordance with a method aspect of this invention a holder for an elongated, flexible medical device having a pair of ends is provided to enable the device to be removed therefrom for introduction into the body of a living being to be exposed to a fluid therein. The holder comprises an enclosed member having a continuous arcuate raceway therein and an access port in communication with the raceway. The method entails coiling the elongated medical device in the arcuate raceway so that one end portion of it extends out of the access port. The device is withdrawn from the holder by one end portion of the device and the device is introduced into the body of a being to perform some medical procedure, whereupon it is exposed to a body fluid. After completing the procedure one of the end portions of the device is inserted in the access port to thread the device back into the raceway of the holder for safe disposal of the holder and the device.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein:

FIG. 3 is an enlarged, transverse sectional view taken along the line 3—3 of FIG. 1;

FIG. 4 is an enlarged, transverse sectional view taken along the line 4—4 of FIG. 1;

FIG. 5 is an enlarged, transverse sectional view taken along the line 5—5 of FIG. 1;

FIG. 6 is an enlarged, transverse sectional view taken along the line 6—6 of FIG. 1;

FIG. 8 is an enlarged isometric view taken from the top of the guide-wire holder of this invention wherein the guide-wire is shown being threaded from the holder into a conventional introducer (shown by phantom lines); and FIG. 9 is an enlarged isometric view taken from the bottom of the guide-wire holder of the package shown in FIG. 1.

DETAILED DESCRIPTION OF THE PREFERRED EMBODIMENT

Figure 1:
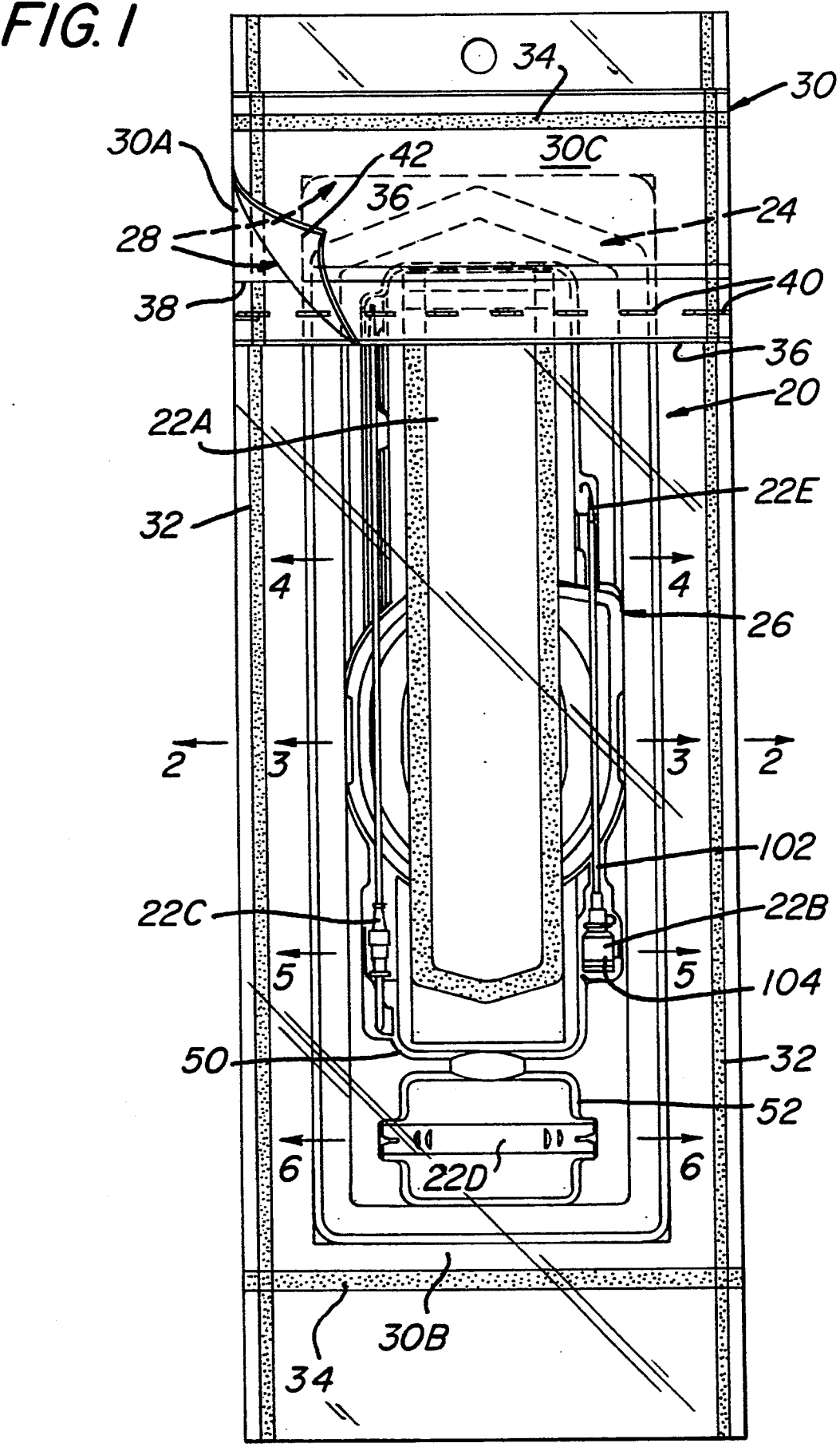
FIG. 1 is a plan view of a sterile package constructed in accordance with the subject invention shown disposed within a sealed pouch.

Referring now in greater detail to the various figures of the drawings wherein like reference characters refer to like parts, there is shown at 20 in FIG. 1 a sterile package constructed in accordance with this invention. The package of this invention is particularly suited for holding various medical components to be used under sterile conditions, e.g., in a catheterization laboratory, in an operating room, in an emergency room, etc.

Figure 2:
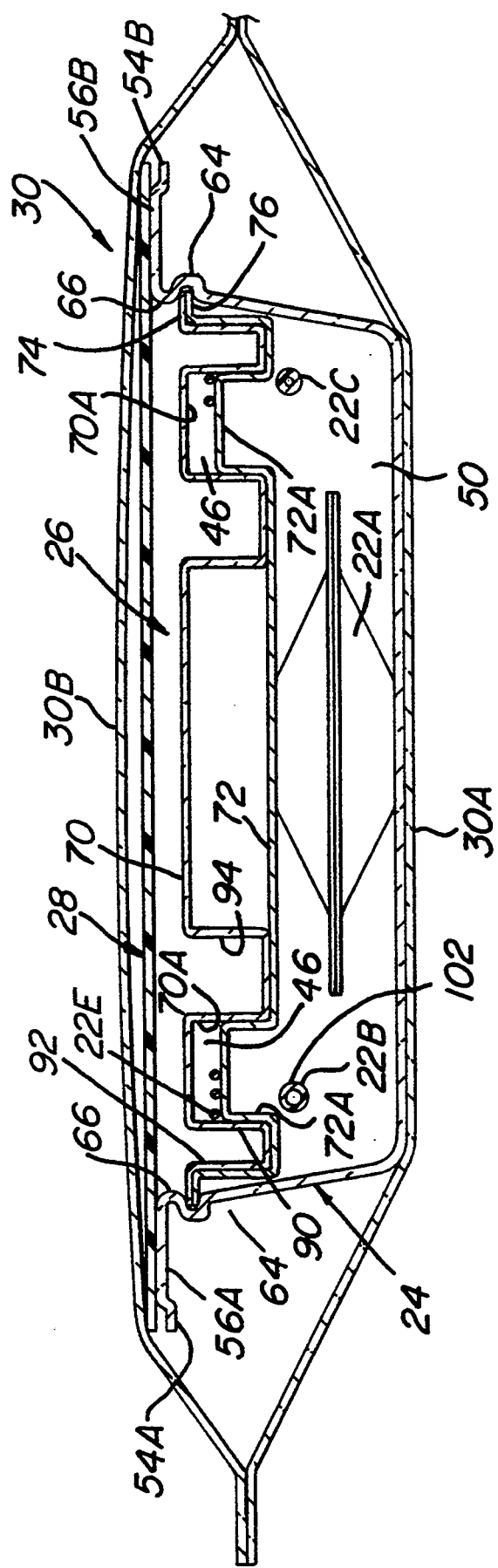
FIG. 2 is an enlarged, transverse sectional view taken along the line 2—2 of FIG. 1.
Figure 7:
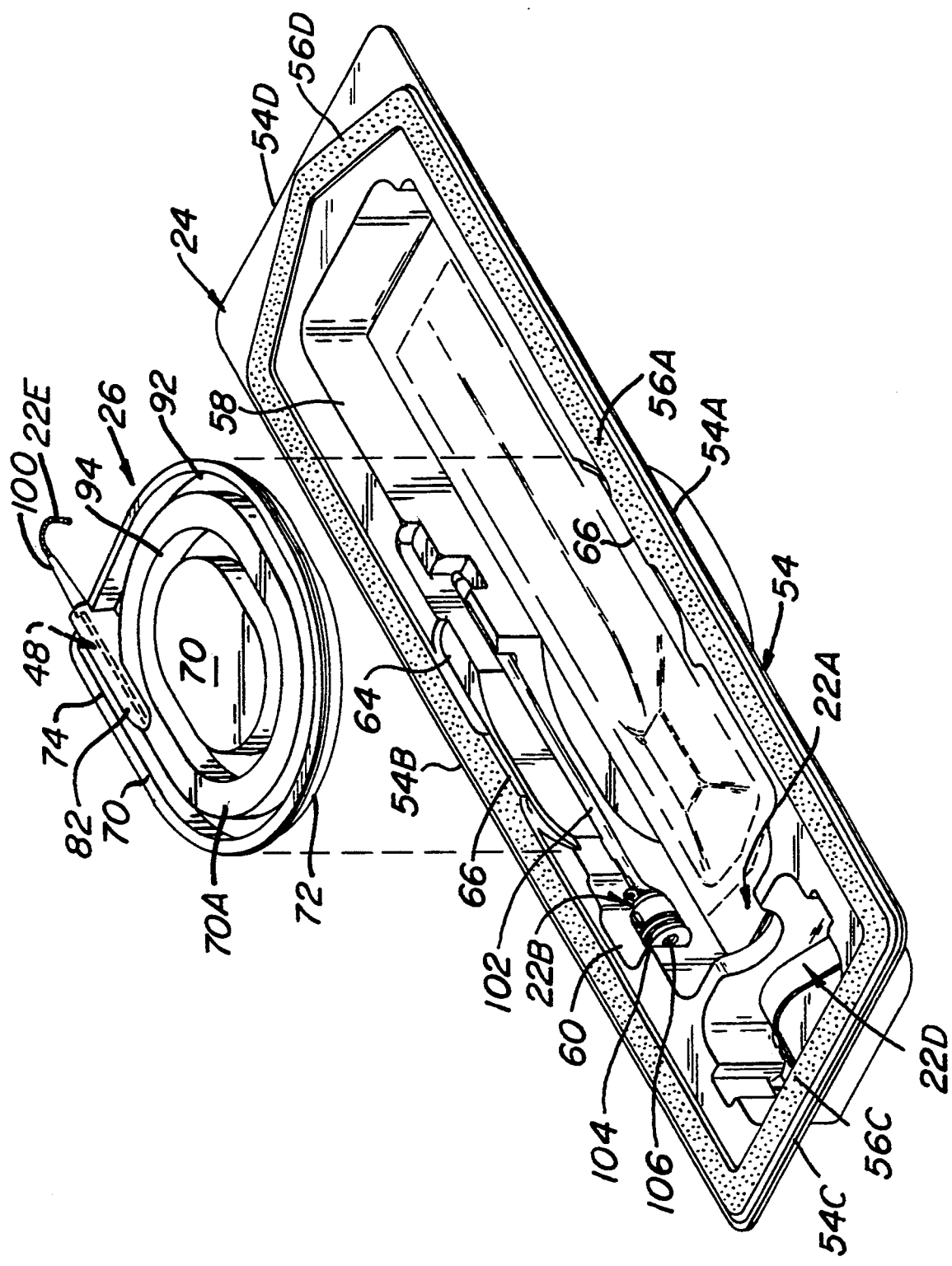
FIG. 7 is a reduced, exploded isometric view of a portion of the package of FIG. 1 after its cover has been removed therefrom to expose its guide-wire holder and other medical components.

In the embodiment of the invention shown herein the package is shown containing one exemplary set of medical components, e.g., a system for hemostatically sealing a percutaneous incision or puncture in an artery, such as the femoral artery, which is accessed for some intravascular catheterization procedure. That exemplary system is disclosed in copending U.S. patent application Ser. No. 07/000,000 filed on Jun. 4, 1993 entitled Hemostatic Vessel Puncture Closure With Filament Lock, assigned to the same assignee as this invention, and whose disclosure is incorporated by reference herein. For the purposes of the description of the invention to follow the components of the system held within the package 20 comprise a hemostatic vessel puncture closure and the deployment instrument therefor which are packaged together within a foil pouch 22A (FIGS. 1-5, and 7), an introducer 22B (FIGS. 1-5 and 7), a blood vessel wall locating device 22C (FIGS. 1-5), a tension spring 22D (FIGS. 1, 2, 6, and 7), and a guide-wire 22E (FIGS. 1, 2 and 7). The blood vessel wall locating device is disclosed in copending U.S. patent application Ser. No. 07/955,095 filed on Oct. 1, 1993, entitled Vessel Position Locating Device and Method of Use, assigned to the same assignee as this invention, and whose disclosure is incorporated by reference herein.

It must be pointed out at this juncture that the package 20 can be used to hold other medical components than the exemplary blood vessel puncture closure system, particularly if one of those components comprises a long, flexible member, e.g., a guide-wire, a catheter, etc.

Turning now to FIGS. 1, 2 and 7 it can be seen that the package 20 basically comprises a hollow, generally rectangular tray 24, a holder 26 for the guide-wire 22E (or another long flexible component), and a generally rectangular cover 28. The details of these elements of the package will be described later. Suffice it for now to state that the tray 24 includes a recess for releasably securing the holder 26 with the guide-wire 22E therein, and a plurality of recessed areas for holding the components 22A-22D, so that when the components are in place in their recesses and the holder is in place in its recess, all of the components making up the vessel closure system are held in place. The cover 28 is releasably secured, e.g., heat sealed, onto a peripheral lip or flange (to be described later) of the tray to complete the package 20, and hence seal the medical components and the holder under sterile conditions therein.

The holder 26, as will be described later, is itself a sealed member and is of simple and low cost construction, which is easy to manufacture and assemble. The holder 26 includes an oval raceway 46 (FIGS. 2 and 7-9) which is arranged to hold the guide-wire 22E in it so that the guide-wire is in a compact, e.g., coiled, condition. The holder includes an outlet passageway or port 48 (FIG. 7) through which the distal end of the guide-wire extends. The guide-wire 22E shown herein is a conventional device having a generally J-shaped distal free end on which a conventional J-straightener 100 is located. The J-straightener 100 is slidably mounted on the distal portion of the guide-wire so that it can be slid over the J-shaped tip to straighten the tip out. This enables the distal end of the guide-wire to be inserted into and through the hemostasis valve of the introducer 22B as shown in FIG. 8 and which will be described later. As will also be described in detail later the port 48 in the holder 26 holds the J-straightener therein so that the linearized distal free end of the guide-wire can be readily inserted into the introducer 22B. Once that has been achieved the guide-wire can be threaded out of the holder 26 and through the introducer to the desired intravascular position within the patient. After use the guide-wire 22E can be readily removed from the patient's body and its proximal end inserted through the port 48 into the raceway 46. The guide-wire can then be threaded into the holder's raceway so that it recoils therein. This action effectively repacks the guide-wire in the sealed holder 26 so that it is ready for easy and safe disposal. This later feature is of considerable importance since it reduces the risk of contaminating others with a blood-coated, guide-wire. Another advantage of the holder 26 is that it enables bulk gamma ray sterilization of the guide-wire 22E held therein.

In order to ensure that the entire package 20 is sterile, so that it will not contaminate the catheterization laboratory, operating room, or other sterile environment where the medical components are to be used, the package 20 is itself sealed within a conventional, sterilizable sack or pouch 30. That pouch, can be seen clearly in FIGS. 1 and 2 and basically comprises a base panel 30A, formed of any suitable flexible plastic material (e.g., a 10% nylon, 90% polyethylene co-extrusion), a cover panel 30B formed of the same material as the base panel, and a header panel 30C formed of a strong, tear resistant material (e.g., TYVEK polymer sold by E. I. duPont de Nemours, Co.). The cover panel 30B and the header panel 30C are disposed over the base panel and are heat sealed to one another along peripheral heat seal lines 32 and 34, with the bottom edge 36 of the header panel overlying the top edge 38 of the cover panel, to form a hollow interior in which the package 20 is located. A line of heat seals 40 is provided across the width of the pouch 22 where the header panel overlies the cover panel to seal the bottom edge of the header panel to the top edge of the cover panel, thereby sealing the package 20 within the pouch.

The pouch 22 is arranged to be opened when it is within a sterile environment, e.g., a cardiac catheterization laboratory, by the user grasping a corner 42 of the header panel 30C and peeling it off of the cover panel 30B, thereby providing an open mouth to the interior of the pouch 22, so that the package 20 can be removed through that mouth. The package 20 can then be placed on a table top 44 (FIG. 3) until the medical components held therein are to be used. To provide access to those components the cover 28 of the package 20 is peeled off of the tray 24. The details of the manner in which the components 22A-22E are removed from the tray will be set forth later. Suffice it for now to state that such action is effected by inverting the tray 24 over the table 44 and flexing it slightly to release the holder 26 from its recess. This action causes the holder 26 to drop out of the tray onto the table 44. The dropping of the holder out of the tray also releases the components 22A-22C from their respective recesses, whereupon they also drop out of the tray onto the table 44 so that they may be used as desired.

As will also be described later, the tension spring 22D is held within its recess in the tray 24 by a pair of opposed, slightly undercut portions. The spring will drop out of the tray automatically upon the dropping of the holder 26, if the flexure of the tray to release the holder also causes portions of the tray adjacent the spring recess to be flexed sufficiently so that the spring is no longer under the undercut portions of the tension spring recess. If not, the tray adjacent the spring recess should be flexed to release the spring from under the undercut portions of the tray at that recess, so that the spring falls out.

Referring now to FIGS. 2-7 the details of the tray 24 will now be described. Thus, as can be seen the tray 24 is an elongated rectangular member which includes a pair of cavities 50 and 52 therein and a peripheral flange 54. The flange includes a pair of long sides 54A and 54B, and a pair of short sides 54C and 54D. The flange sides 54A and 54B include raised linear ridges 56A and 56B, respectively, extending continuously therealong. The flange side 54C includes a continuous linear ridge 56C extending therealong. The flange side 54D includes a continuous chevron shaped ridge 56D extending therealong. The cover 24 is releasably secured, e.g., heat sealed, to the base along the ridges 56A-56D. As will be appreciated by those skilled in the art with the cover sealed to the base along the ridges the corners of the cover 24 immediately adjacent the ends of the chevron portion of the ridge can be readily lifted up to provide a grasping tab for peeling the cover off of the tray.

The cavity 50 is of generally rectangular shape and includes a central, rectangular recess 58 (FIG. 4) and a pair of side recesses 60 and 62. The central recess 58 is contoured to the outer profile of the component 22A to hold that component therein. The side recesses 60 and 62 are contoured to the outer profile of the components 22B and 22C, respectively, to hold those components therein. Overlying the recesses 58, 60, and 62 is a recess 64 which is contoured to the outer profile of the holder 26 to hold it therein. A pair of tabs or ears 66 (FIGS. 1 and 2) extend over the recess 64 on opposite sides thereof so that they overlie the holder 26 when it is located within the recess 64 to releasably secure the holder in place. With the guide-wire holder 26 in place it overlies the components 22A, 22B, and 22C, in the recesses 58, 60, and 62, so that those components do not move about.

The cavity 52 is also of a generally rectangular shape, but is smaller than the cavity 50. The cavity 52 serves as the recess for holding the spring 22D therein. As noted earlier the spring is retained within its recess by a pair of undercut portions. Those portions are shown in FIG. 6 and designated by the reference numbers 68. Thus, as can be seen therein when the spring is located within the cavity 52 its ends are located within the undercut portions 68. This action holds the spring in place.

In accordance with a preferred embodiment of this invention the tray is formed of a self-supporting material so that it retains its shape in order to ensure that the components do not shift about within the package 20 after it is sealed, yet which is still somewhat flexible so that it can be flexed to release the guide-wire holder and the tension spring. For example, the tray and the holder are each formed of a clear 0.030 mils, uncoated gamma sterilizable polyethylene terephthalate. That material offers the advantages of being recyclable, easy to sterilize, easy to manufacture, and non-reactive with the materials making up the medical components held in the package 20.

It should be pointed out at this juncture that while it is desirable to utilize contoured cavities or recesses within the interior of the tray to hold like-shaped components in place in the package, such an arrangement is not mandatory. Thus, it is contemplated that the tray merely include a recess to releasably hold the holder 26 therein and another cavity, without any contoured recesses, so that the components 22A-22D can be held therein, either free to move about, or releasably secured in place by other securing means, e.g., tape, adhesive, etc.

Referring now to FIGS. 1, 2, and 7-10 the details of the guide-wire holder 26 will now be considered. Thus, as can be seen that holder 26 basically comprises a top section 70 and a bottom section 72. The sections 70 and 72 are preferably molded of the same material as that of the tray. The sections are generally planar members and include flat oval shaped recesses 70A and 72A, respectively, therein. The recesses are identical in shape, except that the recess 72A is slightly larger and its depth slightly greater than that of the recess 70A. The top section 70 is secured to the bottom section 72 by the recess 70A being disposed within the recess 72A so that there is frictional engagement between the sidewalls of the top section forming the recess 70A and the sidewalls of the bottom section forming the recess 70B. Since the recess 72A is slightly larger and deeper than the recess 70A when the two sections are secured together they form the flat oval annular space or raceway 46 between them.

The outer periphery of the section 70 is a flange 74 and the outer periphery of the section 72 is a flange 76. The flanges abut each other when the two sections 70 and 72 are secured together.

It should be pointed out at this juncture that the sections 70 and 72 need not be separate components, like shown herein. Rather they may be initially secured together along a corresponding side by a living hinge (not shown) so that the two sections may be folded together along that hinge, whereupon the recesses of those sections frictionally engage each other to complete the assembly and form the arcuate raceway 46 therebetween. Moreover, the two sections 70 and 72 may be secured together by means other than the frictional engagement of their recess, e.g., by an adhesive between their peripheral flanges.

The sections 70 and 72 have respective obtuse angled corners 78 and 80 which overlie each other when the sections are secured together. The corner 80 of the section 72 includes a long, straight semi-circular recess 82 extending from the interior of its recess 72A to the outer edge of its flanged periphery 76. The corner 78 of the section 70 includes a short straight semi-circular recess 84 extending from the interior of its recess 70A to the outer edge of its flanged periphery 74. The semi-circular recesses 82 and 84 conjoin to form the access port 48 when the holder's two sections 70 and 72 are secured together.

As mentioned earlier the port 48 serves as the accessway to the interior of the holder so that the guide-wire can be withdrawn therefrom or inserted therein, as the case may be. To that end the port 48 is shaped to accommodate the proximal portion the conventional J-straightener 100 therein but will not allow the distal portion of the straightener to enter into the holder, for reasons to be apparent from the discussion of the use of the holder 26.

As can be seen in FIG. 9 the section 72 includes a second flat oval shaped recess 90 extending about almost all of its periphery close to the peripheral flange 76. The recess 90 shares a common sidewall with the recess 72A. As can be seen in FIG. 8 the section 70 also includes a second flat oval shaped recess 92 extending about almost all of its periphery close to the peripheral flange 74. The recess 92 shares a common sidewall with the recess 70A. The recess 92 is arranged to be disposed and frictionally engaged within the recess 90 when the two sections are secured together to further enhances the securement of those sections and thereby prevent accidental disconnection. The section 70 also includes a third recess 94. This recess is also of flat oval shape and is located centrally of the recess 70A and shares a common sidewall therewith.

The removal of the components 22A–22E from the package is as follows: The cover 28 is removed by grasping a corner of it adjacent an end of the chevron ridge and by peeling the cover completely off of the tray 24. The tray is then inverted and its long sides pulled apart in the direction of the curved arrows shown in FIG. 3, whereupon the ears or tabs 66 which had been disposed over the holder 26 move away from the edge of the holder by the slight distance shown in FIG. 3, so that the holder is released from its recess 64 and it drops thereout onto the table 44. This action frees the components 22A–22C and 22D, whereupon these components also drop out of the tray and onto the table 44. If the flexure of the tray as described above does not release the spring 22D from its cavity, such action can be readily effected by flexing the tray adjacent that cavity to free the ends of the spring from the undercut portions 68, as described above, so that the spring will drop out when the tray is inverted.

The guide-wire 22E is arranged to be readily removed from the holder 26 for introduction through any conventional introducer, such as the introducer 22E. That introducer includes an elongated tubular distal portion 102 Which extends into the patient's vascular system and a cylindrical proximal body portion 104 in which the hemostasis valve (not shown) is located. A entry port 106 (FIG. 7) is located within the proximal end face of the body portion 104. With the J-straightener 100 located within the access port 48, as described earlier, the guide-wire 22E and/or the J-straightener 100 is manipulated so that the free distal end of the guide-wire, which naturally assumes a J-shape, is located within the straightener, as shown in FIG. 8. This action straightens or linearizes the J-shaped distal end of the guide-wire so that it can be inserted through the entry port 106 into the introducer body 104. This is accomplished by the user holding the holder 26 within his/her palm so that the corner with the access port 48 having the J-straightener 100 therein is located immediately adjacent the thumb and index finger of the hand holding the holder. The J-straightener 100 is then grasped by those fingers and pushed through the entry port 106 in the introducer and through the introducer's hemostasis valve. This action causes the J-straightener to be retained within the hemostasis valve. The holder 26 with the guide wire 22E therein can then be retracted slightly from the introducer 22B, thereby unreeling a short length of the guide-wire from the holder, so that a portion of the guide-wire is exposed between the introducer and the holder's access port 48. This exposed portion of the guide-wire can then be grasped between the user's index finger and thumb to feed the guide-wire into and through the introducer 22B. The feeding procedure is repeated until the guide-wire passes through introducer into the desired position within the patient's vascular system. The introducer can then be removed and the guide-wire used for its desired purpose.

After use the blood-soaked guide-wire 22E can be readily reinserted into the holder 26 for convenient and safe disposal. To that end the proximal end of the guide-wire 22E is inserted into the access port 48 in the holder 26 and is threaded into the communicating annular raceway 46 until the entire guide-wire is within the holder, i.e., most of the guide-wire being in the raceway and only the distal end being in the access port.

As should be appreciated the recesses in the sections 70 and 72 forming the holder provide a convenient, slip-resistant site to grasp the holder 26 in the user's hand to prevent it from slipping out of the grasp when the guide-wire is being fed into or out of the holder 26.

Without further elaboration the foregoing will so fully illustrate my invention that others may, by applying current or future knowledge, adopt the same for use under various conditions of service.

What is claimed is:

1. In combination a sterile holder and an elongated, flexible medical device, said device having a small cross sectional diameter, said holder holding said device therein in a coiled configuration and comprising an upper section and a lower section, each of said sections being generally planar and having an arcuate recess therein, said sections being secured together with the recess of one of said sections being disposed within the recess of the other of said sections to form a continuous annular raceway between said sections, said raceway having arcuate wall portions spaced apart from each other and an access port in communication with the ambient surroundings and being larger in diameter than the diameter of said device to enable said device to be introduced through said access port and into said annular raceway, whereupon said arcuate wall portions guide said device to coil up within said raceway.

2. The holder of claim 1 wherein said sections are each formed of a plastic material.

3. The holder of claim 2 wherein said sections are held together by the frictional engagement of said recesses to each other.

4. The holder of claim 1 wherein said sections are held together by the frictional engagement of said recesses to each other.

5. The holder of claim 4 wherein said device comprises a guide-wire having a J-shaped distal end on which a straightening member is disposed to straighten said tip to enable said guide-wire to be inserted into an introducer extending into the body of said being, said straightening member being generally linear, and wherein said access port is elongated and of sufficient diameter to accommodate a portion of said member therein to hold said distal end of said guide-wire in a generally linear orientation to facilitate introduction into said introducer.

6. The holder of claim 1 wherein said device comprises a guide-wire having a J-shaped distal end on which a straightening member is disposed to straighten said tip to enable said guide-wire to be inserted into an introducer extending into the body of said being, said straightening member being generally linear, and wherein said access port is elongated and of sufficient diameter to accommodate a portion of said member therein to hold said distal end of said guide-wire in a generally linear orientation to facilitate introduction into said introducer.

7. A sterile package comprising a tray, a cover, a holder, and an elongated flexible medical component for use in the body of a being to be exposed to a body fluid, said tray having a hollow interior portion with a flange extending thereabout, and plural retaining members located adjacent said hollow interior portion, said holder comprising a sealed member having an annular raceway therein holding said elongated flexible medical component in said holder in a compact coiled configuration, said holder being releasably secured to said tray by said retaining members, said cover including a peripheral portion arranged to be releasably secured to said peripheral flange of said tray and over said holder, said tray being flexible to enable it to be flexed to release said holder from said retaining members after said cover is removed from said tray, whereupon said holder is freed so that said elongated flexible medical component can be removed from said holder without opening said holder.

8. The package of claim 7 wherein each of said retaining members comprises a tab projecting inwardly toward said hollow interior portion, with said tabs being disposed over respective portions of said holder, thereby releasably securing said holder to said tray.

9. The package of claim 8 wherein said pair of retaining members are disposed on opposite sides of said hollow interior portion.

10. The package of claim 9 wherein said interior portion includes a recess configured to the shape of said holder for receipt of said holder therein.

11. The package of claim 10 additionally comprising a second medical component, and wherein said tray includes a second recess having a shape generally corresponding to a portion of the exterior contour of said second component for holding said second component in place in said tray.

12. The package of claim 11 wherein said package is formed of a plastic material.

13. The package of claim 7 wherein said cover is heat sealed to said tray.

14. The package of claim 7 wherein said elongated flexible medical component has a small cross sectional diameter, and wherein said holder comprises a generally flat member having a continuous annular raceway including arcuate wall portions spaced from each other and an access port to said raceway, said access port being larger in diameter than the diameter of said elongated flexible medical component to enable said elongated flexible medical component to be introduced through said access and into said annular raceway, whereupon said arcuate wall portions guide said elongated flexible medical component to coil up within said raceway.

15. The package of claim 14 wherein said holder comprises a pair of generally planar sections each comprising an arcuate recess therein and secured together, with one of said recesses being located in the other of said recesses to form said annular raceway therebetween.

16. The package of claim 15 wherein said sections are each formed of a plastic material.

* * * * *